United States Patent
Schnakenberg et al.

(10) Patent No.: US 6,443,893 B1
(45) Date of Patent: Sep. 3, 2002

(54) DEVICE FOR MEASURING THE INTRA-OCULAR PRESSURE

(75) Inventors: Uwe Schnakenberg, Aachen (DE); Wilfried Mokwa, Krefeld (DE); Christine Kreiner, München (DE); Horst Richter, Würselen (DE)

(73) Assignees: Acritec GmbH, Glienicke (DE); Mesotec Gesellschaft für Medizinische Sensortechnik mbH, Hannover (DE)

( * ) Notice: Subject to any disclaimer, the term of this patent is extended or adjusted under 35 U.S.C. 154(b) by 0 days.

(21) Appl. No.: 09/462,182
(22) PCT Filed: Jul. 1, 1998
(86) PCT No.: PCT/EP98/04072
§ 371 (c)(1), (2), (4) Date: Apr. 24, 2000
(87) PCT Pub. No.: WO99/01063
PCT Pub. Date: Jan. 14, 1999

(30) Foreign Application Priority Data

Jul. 1, 1997 (DE) .......................................... 197 28 069

(51) Int. Cl.⁷ .............................. A61B 3/16; A61B 5/00
(52) U.S. Cl. ........................................ 600/398; 600/561
(58) Field of Search .................................. 600/398, 399, 600/552, 561; 128/903; 623/4.1, 6.11

(56) References Cited

U.S. PATENT DOCUMENTS

| 4,922,913 A | * | 5/1990 | Waters, Jr. et al. .......... 600/398 |
| 5,005,577 A | | 4/1991 | Frenkel |
| 5,433,701 A | * | 7/1995 | Rubinstein ..................... 604/8 |
| 5,840,041 A | * | 11/1998 | Petter et al. ................. 600/547 |

FOREIGN PATENT DOCUMENTS

DE 43 41 903 A1 6/1995

* cited by examiner

Primary Examiner—Kevin Shaver
Assistant Examiner—Charles Marmor, II
(74) Attorney, Agent, or Firm—Crowell & Moring, LLP

(57) ABSTRACT

A device for measuring intraocular pressure includes a remote measuring device that can be implanted in the eye and that contains a pressure sensor, a device that can convert the sensor signals into information that can be transmitted without wires, and a transmitter. The device also includes a receiving device located outside the eye which receives the information transmitted by the transmitter and which is connected to an evaluation device in which the received information is converted into data on the intraocular pressure for recording.

11 Claims, 1 Drawing Sheet

DEVICE FOR MEASURING THE INTRAOCULAR PRESSURE

The invention relates to a device according to the preamble of claim 1. A device of this kind is in known from U.S. Pat. No. 5,005,577.

Measurements of intraocular pressure (glaucoma) are normally conducted on a routine basis during a visit to an eye specialist. In patients with known glaucoma, pressure measurements are performed at regular intervals of 6 to 12 weeks. These pressure measurements however are not very informative since the intraocular pressure varies with time of day. To obtain objective information as to whether a pathological pressure situation exists, continuous pressure measurements must be performed over a long period of time and a decision can be made on their basis as to whether therapy should be initiated, and what kind. This is not possible with the devices currently available for measuring intraocular pressure (tonometers).

The available tonometers (applanation and impression tonometers) permit an exact determination of the intraocular pressure (Grehn, F., Leydhecker, W. "Augenheilkunde" [Ophthalmology], 26th edition, Springer Verlag, pp. 244–5). Their practical reliability for routine early detection is limited, however. With the known measuring devices, the cornea of the eye which is sensitive to pain is touched during measurement so that pressure measurement can be performed only following local anesthesia of the eye. The known measuring devices provide values that can not be used, when the surface of the cornea is abnormal as a result of edema or scars or in astigmatism. Investigations following operations on the eye to monitor the success of the operation are not possible. Non-contact clinometers currently on the market do not achieve the measurement accuracy required for a reliable diagnosis. Especially in the high pressure range which results in irreversible damage to the optic nerves, measurements with the currently available non-contact tonometers are too inaccurate and unreliable. Since the applanation of the cornea is used for measurement in these clinometers as well, they suffer from the disadvantages associated with this applanation.

The device described at the outset known from U.S. Pat. No. 5,005,577 includes a remote measurement device that can be implanted in an eye using an intraocular lens, said device containing a pressure sensor, a device that converts the sensor signals into information that can be transmitted without wires, and a transmitter. By means of a receiver located outside the eye, the information transmitted by the transmitter that can be implanted is received and converted into data on the intraocular pressure that can be recorded. In addition, the known device can have an energy source supplied from outside, for example a photoelectric element, to produce an active sensor and telemetric transmitter for data transmission.

In order to perform objective evaluation as to whether a pathologic optical situation exists in the eye, pressure measurements must be evaluated that cover a long period of time. Acquisition of these long-term pressure measurements is cumbersome with the known devices.

Hence the goal of the invention is to provide a device for measuring intraocular pressure with which an elevated intraocular pressure (glaucoma) can be monitored continuously and called up as necessary.

This goal is achieved according to the invention by the characterizing feature of claim 1.

Using the data logger in the implanted remote measurement device, continuous recording and storage of the measured values are performed over a long period of time. These data can be called up as necessary within a short space of time, for example within seconds to minutes. It is only during this period of time that an auxiliary device, in the form of a manual device, spectacles, or an eye bandage must be used to receive the measured data.

The remote measuring device which is preferably designed for active telemetry can be located at a suitable point, for example the sulcus of the capsule or the anterior chamber, as an implant that can be installed by surgery. This implant can be in the form of an intraocular lens, with the remote measuring device being provided outside the optical part of the lens, preferably at a haptic margin surrounding the lens part. This creates an intelligent lens for multifunctional measured value acquisition by active telemetry and integration of the data logger by which measured values can be stored.

Suitable sensors are those that allow determination of the intraocular pressure. In particular, the pressure sensor or pressure sensors, in contrast to the known capacitive measuring sensors (Sensors and Actuators A, 37–38 (1993) 93–105) can be created using surface micromechanics. In addition, electrodes for stimulation and derivation of stimulus potentials can be provided. The pressure sensor, the corresponding signal processing circuit, the data logger, and the telemetry components in the sensor, especially the coil and capacitors, are preferably integrated monolithically in a chip, for example a silicon chip. By inductive signal and energy transmission between the implanted remote measuring device and the receiving device provided outside the eye, active telemetry is obtained with the power supplied to the remote measuring device in the eye by inductive energy transmission. For this purpose, both the implanted remote measuring device and the receiving device located outside the eye have suitably designed antennas in the form of coils (ring coils).

Continuous measurement of intraocular pressure over several stages is possible without continuous data callup to the outside being necessary. With the data logger integrated into the active telemetry, data can be stored and called up at specific times, once a week for example. The implanted sensors can be calibrated without an external device, using self calibration. No spectacles need be worn for calibration. The energy supplied is reduced in active telemetry. Interference with the measurement is reduced by the monolithically integrated design. The measuring device is EMV tolerant. With a preferred surface micromechanical solution, the likelihood of the sensors breaking is reduced. In addition, surface-micromechanical sensors can be made in that sizes required for implantation. With the monolithically integrated design, silicon chips can be made thin enough to fit in the eye implant, especially an intraocular lens. The power can be supplied by inductive energy transmission from outside so that no battery is required.

One embodiment of the invention will now be explained in great detail with reference to the figures.

Figure 1:
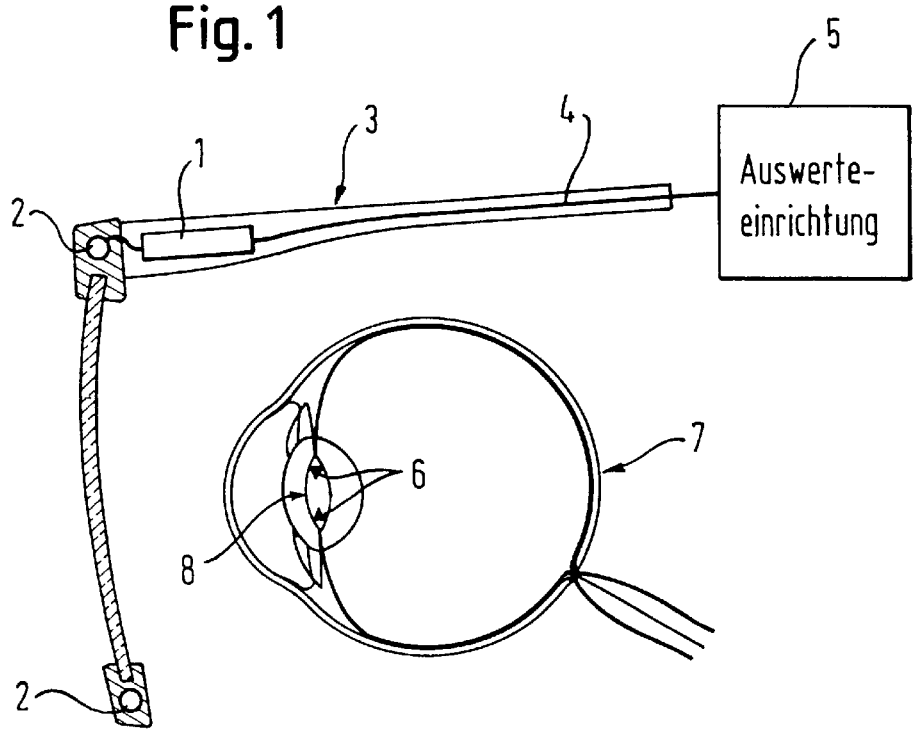
FIG. 1 is a schematic side view of an embodiment of the invention.
Figure 2:
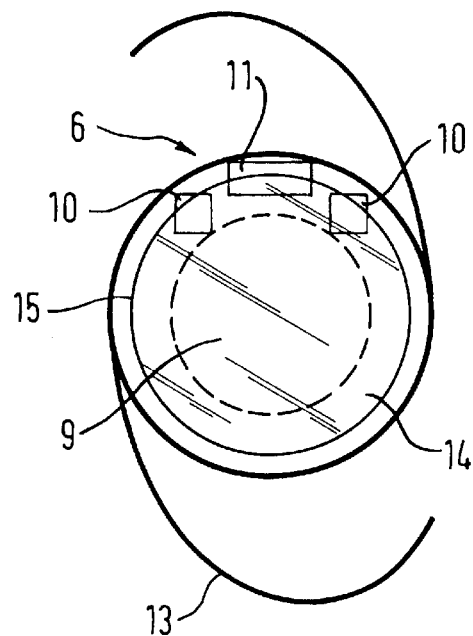
FIG. 2 shows an implant designed as a lens which contains the remote measuring device used in the invention.
Figure 3:
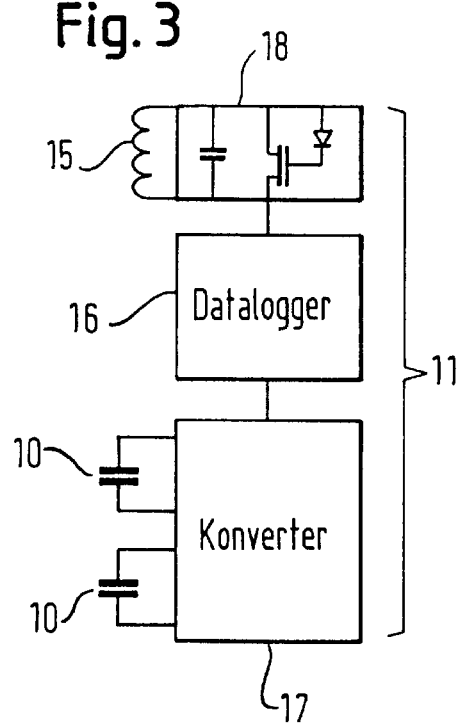
FIG. 3 is a block circuit diagram of the implanted remote measuring device.

In the embodiment shown in the figures, a remote measuring device 6 is placed in the eye as an eye implant designed as an intraocular lens 8. Remote measuring device 6 which contains pressure sensors 10 and sensor telemetry components, especially telemetry electronics 11, is located in the vicinity of a haptic margin 14 surrounding an optical part 9 of the intraocular lens. Pressure sensors 10 can be designed using surface micromechanics. Telemetry electronics 11 contain a data logger 16 to store the measured values received from pressure sensors 10. In addition, the telemetry electronics is connected with a coil 15 that operates as a transmitting and receiving antenna. The measured data stored in data logger 16 can be called up and sent if necessary by activating an electronic switch in a transmission circuit 18 connected with coil 15. Telemetry electronics 11 as well as pressure sensors can be integrated monolithically into a silicon chip made so that it fits in the haptic margin 14 of the lens. Preferably the lens is made of silicon material. Haptic margin 14 has a width of approximately 1 mm. The lens diameter can vary between 6.5 and 7 mm. The intraocular lens can be secured for example in the capsule of the eye using haptic threads 13. Pressure sensors 10 (sensor components) and the telemetry electronics (read station) with the transponder electronics and the micro-antenna designed as a coil 15 are in the haptic margin 14 outside the optical zone 9 of the intraocular lens. The thickness of the lens body depending on the refractive power can be 1 to 2 mm.

A polydiorganosiloxane, preferably, is used as the implant material because of its good biocompatibility and deformability. The implant can thus be implanted in the folded or even rolled state through a small incision. A polydiorganosiloxane, especially polydimethylsiloxane, can be used for encapsulation of the microcomponents of the remote measuring device.

The measurement signals generated by pressure sensors 10 as a function of the measured intraocular pressure are converted by the telemetry and transponder electronics into information that can be transmitted without wires in a converter 17 and transmitted by means of the micro-antenna designed as coil 15 and received outside the eye by a receiving device 1 through an antenna likewise designed as a coil 2. Receiving device 1 and coil 2 can be located in a spectacle frame 3. However, other securing means are also suitable, for example a comfortable eye bandage. Receiving device 1 is connected by a cable 4 with an evaluating device 5 in a base unit. This base unit can have a battery for power supply in addition to the evaluation and interface electronics. However it is also possible to provide the energy through a power cable. Evaluation unit 5 converts the received information into data that can be recorded. For this purpose, a fixed data evaluation device can be provided for off-line data processing, storage, analysis, and display on a PC.

The power for the remote measuring device 6 implanted in the eye can be provided by induction through the two coils 2 and 15 that act as antennas during transceiver operation.

What is claimed is:

1. A device for measuring intraocular pressure comprising:

a remote measuring device adapted to be implanted in an eye, said remote measuring device having a pressure sensor, a converter for converting sensor signals into information for wireless transmission, and a transmitter;

a receiver adapted to be located outside the eye for receiving information transmitted by the transmitter; and an evaluation device for converting information received into data expressing the intraocular pressure and for recording the data, wherein the remote measuring device further includes a data logger in which measurement data continuously supplied by said pressure sensor is stored and from which the measurement data is called up at certain times in operation of the converter.

2. The device according to claim 1 wherein the remote measuring device is located in or on an implant.

3. The device according to claim 2 wherein the implant is an intraocular lens.

4. The device according to claim 3 wherein the remote measuring device is located outside an optical lens part of the lens.

5. The device according to claim 2 wherein the implant is made of a polydiorganosiloxane.

6. The device according to claim 5, wherein said polydiorganosiloxane is polymethylsiloxane.

7. The device according to claim 1 wherein the pressure sensor is designed using surface micromechanics.

8. The device according to claim 1 wherein a polydiorganosiloxane is used for encapsulation of microcomponents forming said remote measuring device.

9. The device according to claim 8, wherein said polydiorganosiloxane is polymethylsiloxane.

10. The device according to claim 1 wherein the pressure sensor, the data logger, and associated signal processing and telemetry components are fully monolithically integrated.

11. The device according to claim 10, wherein said telemetry components include a coil and capacitors.

* * * * *